United States Patent
Grundei

(10) Patent No.: US 7,771,485 B2
(45) Date of Patent: Aug. 10, 2010

(54) BALL JOINT OR CAP IMPLANT FOR AN ARTIFICIAL HIP JOINT

(75) Inventor: Hans Grundei, Lübeck (DE)

(73) Assignee: ESKA Implants GmbH & Co., KG, Lubeck (DE)

( * ) Notice: Subject to any disclaimer, the term of this patent is extended or adjusted under 35 U.S.C. 154(b) by 133 days.

(21) Appl. No.: 12/077,805

(22) Filed: Mar. 20, 2008

(65) Prior Publication Data

US 2009/0112330 A1 Apr. 30, 2009

(30) Foreign Application Priority Data

Mar. 21, 2007 (DE) ........................ 10 2007 014 265

(51) Int. Cl.
*A61F 2/36* (2006.01)
(52) U.S. Cl. ................... 623/23.11; 623/23.12
(58) Field of Classification Search ............... 623/3.12, 623/23.29–23.3, 23.5, 23.551, 22.11, 22.13, 623/22.15, 22.33, 22.4, 23.11, 23.12, 23.19
See application file for complete search history.

(56) References Cited

U.S. PATENT DOCUMENTS

| | | | |
|---|---|---|---|
| 5,879,406 A | 3/1999 | Lilley | |
| 5,916,269 A | 6/1999 | Serbousek et al. | |
| 6,045,581 A | 4/2000 | Burkinshaw | |
| 6,425,921 B1 | 7/2002 | Grundei et al. | |
| 7,578,851 B2 * | 8/2009 | Dong et al. | 623/22.21 |
| 2005/0049716 A1 | 3/2005 | Wagener et al. | |
| 2005/0182494 A1 | 8/2005 | Schmid | |

FOREIGN PATENT DOCUMENTS

| | | |
|---|---|---|
| DE | 197 50 121 C1 | 4/1999 |
| DE | 101 56 610 A1 | 5/2003 |
| DE | 103 18 374 B3 | 1/2005 |
| EP | 1 475 057 A1 | 11/2004 |
| WO | WO 03/044383 A1 | 5/2003 |

OTHER PUBLICATIONS

German language Office Action dated Dec. 5, 2007 issued for corresponding German Patent Application No. 10 2007 014 265.1-35.
European Search Report dated Jul. 28, 2008 issued in corresponding European Patent Application No. EP 08 151 509.0.

* cited by examiner

*Primary Examiner*—David Isabella
*Assistant Examiner*—Marcia Hoffman
(74) *Attorney, Agent, or Firm*—Flaster/Greenberg P.C.

(57) ABSTRACT

A ball joint or cap for an artificial hip joint is described that is suitable for carrying out a rotating or pivoting motion in an artificial hip joint socket, with a gap being provided for a natural fluid film (synovial fluid) between itself and the artificial hip joint socket, and with regular depressions without interconnecting channels between them being recessed in areas of its surface. It is proposed that its surface in the polar area is smooth and without depressions, that an area is provided in an intermediate area between the smooth polar area and its equator, in which depressions are recessed with hole widths between 1.0 mm to 3.0 mm, that adjacently in the intermediate area in the direction of its base edge, further depressions are recessed, the hole widths of which become steadily smaller, the closer they lie to the base edge, with hole widths between 0.5 mm and 1.0 mm.

5 Claims, 1 Drawing Sheet

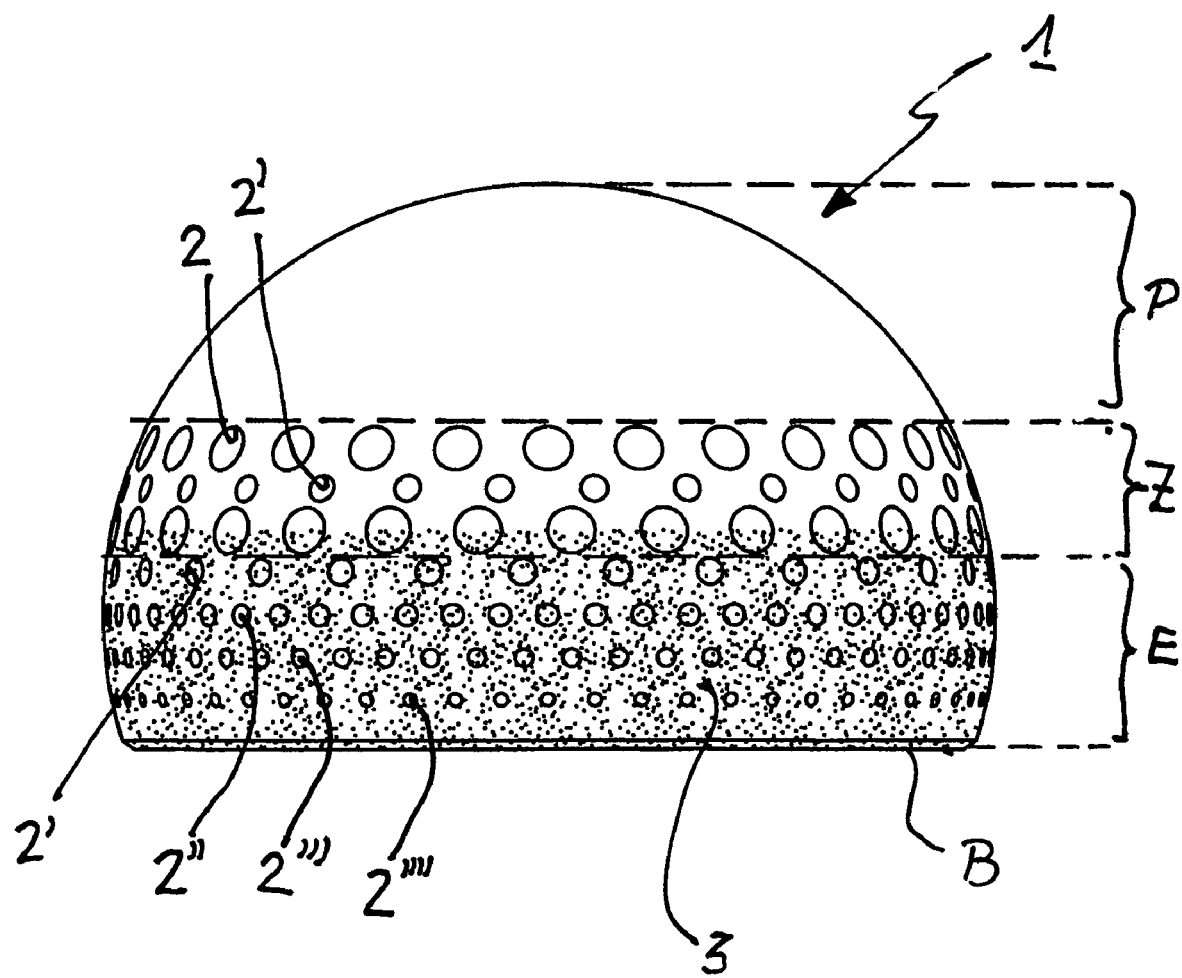

BALL JOINT OR CAP IMPLANT FOR AN ARTIFICIAL HIP JOINT

BACKGROUND OF THE INVENTION

1. Field of the Invention

The present invention relates to a ball joint or cap implant for an artificial hip joint that is suited to carry out a rotating or pivoting motion in an artificial hip joint socket, with a gap being provided for a natural fluid film, the synovial fluid, between the ball joint or cap implant and the artificial hip joint socket, and with regular depressions, without interconnecting channels between them, being recessed in areas of its surface.

2. Description of Related Art

A ball joint of this type is known from DE 103 18 374 B3.

A fundamental problem in artificial hip joints is the friction between the components of the joint, the ball joint and hip joint sockets, which leads in turn to wear and tear that can give rise to medical complications.

The invention of the previously cited document was based on the effort to develop a ball joint or cap in such a way as to achieve a minimization of friction and thus a minimization of wear, with significantly reduced manufacturing costs. To do so, it was proposed that, in a ball joint with at least three grooves running in a circle around the polar axis, the grooves are introduced into the ball joint surface without interconnecting channels between them. In this way, a contact surface minimization is achieved since there is no direct contact between the ball joint and the artificial hip joint socket in the area of the grooves. The grooves running in a circle are filled with synovial fluid after implantation. The grooves do not have a buffering effect herein, but rather they perform a weight-bearing role. In addition, due to the fluid-filled grooves, a vacuum is generated between the ball joint and the hip joint socket that represents in turn a significant luxation inhibitor.

Even though this approach was quite promising, it is to be noted that the lubricant effect of the synovial fluid in the gap between the ball joint and the hip joint socket is not optimally exploited to lubricate the ball joint vis-à-vis the hip joint socket, on the one hand, or to carry away any wear particles.

Against this backdrop, the task of the present invention is to propose a ball joint or cap of the type noted at the outset, in which the lubricating and cleaning effect is significantly enhanced compared to the prior art.

BRIEF SUMMARY OF THE INVENTION

In order to solve this task, it is proposed according to the invention that the surface of the ball joint or cap in the polar area is smooth and without depressions, that an area is provided in an intermediate area between the smooth polar area and the area above its equator, in which depressions are recessed with hole widths from 1.0 mm to 3.0 mm, that in the direction of its other pole, further depressions are recessed, the hole widths of which become steadily smaller the closer they lie to the base edge, with hole widths between 0.5 mm and 1.0 mm.

The surface of the ball joint or cap is therefore structured in a graduated fashion from the intermediate area below the polar area until its base edge, in the sense that, starting from the intermediate area, an initially somewhat rougher structure is provided in the form of the recessed depressions. Moving further out from the equator, there is an area adjacent to the intermediate area below the equator, which is provided with depressions of smaller dimension, which become smaller moving away from the border adjacent to the intermediate area toward the base edge.

In addition, the surface in the area between the equator and the base edge can be structured with depressions having widths between 50 µm and 250 µm, which are produced for example using laser beams.

The surface of the inventive ball joint is therefore divided essentially into three areas. Each one of these areas is adapted to the functions assigned to it.

The smooth polar area is the load-bearing zone of the ball joint, since during walking that is where the largest forces are introduced.

The intermediate area fulfills the function of a reservoir for the synovial fluid and at the same time performs a buffer function. This succeeds because the depressions do not have any kind of interconnecting channels between them, so that the pressure developing in the individual depressions builds up to form a pressure buffer.

The area below the equator serves not only for lubricating the joint, but in particular also for cleaning, i.e. for carrying away any abrasive or other particles. The discrete macroscopic depressions in this area with widths above 0.5 mm serve primarily to lubricate the joint. The microstructures with widths between 50 µm and 250 µm serve primarily to carry away the mentioned particles. This works analogously to the known Lotus effect.

According to an advantageous further development, the macroscopic depressions have a round opening. Due to this design, certain surface pressures of the synovial fluid can be built up in the depressions.

According to yet another advantageous embodiment, it is provided that the depressions are designed to be dome-shaped in cross-section. In this way, they offer, on the one hand, a sufficiently large reservoir for the synovial fluid, and, on the other hand, the possibility of good rinsing and replacement of the synovial fluid stored in the depressions by subsequently flowing synovial fluid.

Yet another advantageous embodiment provides that depressions with alternating hole widths between 1.0 mm and 3.0 mm are recessed into the surface in the intermediate area above the equator. In this way, pressures to be developed can be set in a targeted manner. The arrangement can provide that the depressions with the larger hole widths go around on the surface almost like a wreath. This first wreath can be followed by a second wreath with depressions with smaller hole widths, which in turn can be followed then by a third wreath with depressions with the larger hole widths. But this exact geometric arrangement is not necessarily required. Arrangements of depressions without a strict geometric orientation would also be conceivable. The invention is described in greater detail using an embodiment according to the single drawing diagram.

BRIEF DESCRIPTION OF THE SEVERAL VIEWS OF THE DRAWING(S)

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 shows a schematic side view of the ball joint or cap designed according to the invention.

DETAILED DESCRIPTION OF THE INVENTION

As can be seen, ball joint 1 is designed to be dome-shaped. In polar area P, the surface is perfectly smooth. This section forms the primary load-bearing part of the ball joint. The rest of the surface of ball joint 1 is characterized by a graduated structure.

An intermediate area Z follows adjacent to polar area P in the direction of the equator. Intermediate area Z is characterized by a macrostructure formed by depressions 2 and 2'. As can be seen, larger depressions 2 alternate with smaller depressions 2'; they are positioned in an alternating manner. Depressions 2 and 2' serve primarily to hold a reservoir for the synovial fluid.

Intermediate area Z is followed by an adjacent area E approximately below the equator. Area E is characterized, on the one hand, by macroscopic depressions with hole widths between 0.5 mm and 1.2 mm. These are also used as reservoirs for the synovial fluid. However, the smaller they become, the more they are used for cleaning the synovial fluid. This macrostructure in area E is underlaid by a surface 3, which is indicated in the drawing diagram by the gray marking and is produced by laser beams. This microscopic surface structure primarily serves to clean the transported liquid.

The described structure results in an optimal division of functions between the various areas of the ball joint. Thus it is ensured that the smooth polar area is constantly wet with synovial fluid. Otherwise, abrasion of disastrous proportions would take place there. If nonetheless there should come to be particles in the synovial fluid, they will be conveyed to the outside by the design of the surfaces with the graduated structure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A ball joint or cap for an artificial hip joint that is suitable for carrying out a rotating or pivoting motion in an artificial hip joint socket having a surface, wherein the surface comprises three areas:
   a polar area that is smooth and without depressions;
   an intermediate area between the smooth polar area and approximately an equator of the ball joint or cap, the intermediate area comprising recessed depressions, each depression having a hole width between 1.0 mm to 3.0 mm, and
   a base edge area that is adjacent to the intermediate area in the direction of a base edge of the ball joint or cap, the base edge area having recessed depressions, the depressions having hole widths that become increasingly smaller the closer the depression is to the base edge, wherein the hole widths are between 0.5 mm and 1.0 mm; wherein the recessed depressions are regularly placed on the surface and do not have interconnecting channels between them.

2. The ball joint or cap of claim 1, wherein the surface in the base edge area further comprises depressions having widths between 50 µm and 250 µm.

3. The ball joint or cap of claim 1, wherein the depressions each have a round opening.

4. The ball joint or cap of claim 1, wherein the depressions have a dome-shaped cross-section.

5. The ball joint or cap of claim 1, wherein the recessed depressions of the intermediate area include a first set of depressions having a first hole width alternating with a second set of depressions having a second hole width, wherein the first hole width and the second hole width are between 1.0 and 3.0 mm, but the first hole width and the second hole width are not the same.

* * * * *